United States Patent
Bastide et al.

(10) Patent No.: US 11,587,676 B2
(45) Date of Patent: Feb. 21, 2023

(54) MANAGING HEALTH CONDITIONS USING PREVENTIVES BASED ON ENVIRONMENTAL CONDITIONS

(71) Applicant: International Business Machines Corporation, Armonk, NY (US)

(72) Inventors: Paul R. Bastide, Ashland, MA (US); Vishrawas Gopalakrishnan, Cambridge, MA (US); Piyush Madan, Boston, MA (US); Fang Lu, Billerica, MA (US)

(73) Assignee: MERATIVE US L.P., Ann Arbor, MI (US)

( * ) Notice: Subject to any disclaimer, the term of this patent is extended or adjusted under 35 U.S.C. 154(b) by 190 days.

(21) Appl. No.: 16/654,445

(22) Filed: Oct. 16, 2019

(65) Prior Publication Data

US 2021/0118560 A1 Apr. 22, 2021

(51) Int. Cl.
*G16H 20/30* (2018.01)
*G16H 50/20* (2018.01)
*G16H 40/60* (2018.01)

(52) U.S. Cl.
CPC .............. *G16H 50/20* (2018.01); *G16H 20/30* (2018.01); *G16H 40/60* (2018.01)

(58) Field of Classification Search
CPC ........ G16H 10/60; G16H 50/20; G16H 50/30; G16H 40/63; G16H 40/67; G16H 50/70;

(Continued)

(56) References Cited

U.S. PATENT DOCUMENTS

2012/0029970 A1 2/2012 Stiles et al.
2014/0358581 A1\* 12/2014 Sudharsan .............. G16Z 99/00
705/2

(Continued)

FOREIGN PATENT DOCUMENTS

WO WO-2020069500 A1 \* 4/2020

OTHER PUBLICATIONS

Kowalska, M. "Relationship Between Quality Of Ambient Air And Respiratory Diseases In The Polish Population" WIT Transactions on Ecology and the Environment 207: 195-202. Southampton: W I T Press. (2016) (Year: 2016).\*

(Continued)

*Primary Examiner* — Rachel L. Porter
(74) *Attorney, Agent, or Firm* — Edell, Shapiro & Finnan, LLC

(57) ABSTRACT

A computer system manages a health condition based on conditions of an environment. Health information of a user is analyzed to determine a health condition affected by environmental conditions. One or more events for the user are obtained based on personal information. The environmental conditions for one or more event locations are determined. One or more preventive items are indicated for the user to attend the one or more events in order for the health condition to tolerate the environmental conditions of the one or more event locations. Embodiments of the present invention further include a method and program product for managing a health condition based on conditions of an environment in substantially the same manner described above.

17 Claims, 4 Drawing Sheets

(58) Field of Classification Search
CPC ........ G16H 30/40; G16H 20/30; G16H 20/70;
G16H 10/20; G16H 20/10; G16H 40/20;
G16H 50/50; G16H 80/00; G16H 15/00;
G16H 20/13; G16H 20/60; G16H 50/80;
G16H 70/60; G06Q 30/0203; G06Q
50/12; G06Q 10/04; G06Q 10/063114;
G06Q 10/0639; G06Q 10/101; G06Q
10/103; G06Q 50/02; G06Q 50/10; G06Q
50/16; G06Q 50/22
See application file for complete search history.

(56) References Cited

U.S. PATENT DOCUMENTS

| 2015/0044651 | A1* | 2/2015 | Thomas | G16H 50/20 434/247 |
| 2016/0189039 | A1 | 6/2016 | Leppanen et al. | |
| 2017/0262604 | A1* | 9/2017 | Francois | G16H 10/60 |
| 2018/0372913 | A1 | 12/2018 | Smoliak et al. | |
| 2019/0088366 | A1* | 3/2019 | Vaughan | G16H 10/20 |
| 2019/0371460 | A1* | 12/2019 | Gutierrez | A61B 5/7282 |

OTHER PUBLICATIONS

"Heat and People with Chronic Medical Conditions", https://www.cdc.gov/disasters/extremeheat/medical.html, Jun. 19, 2017, 2 pages.
"Heat As A Seizure Trigger", Sep. 11, 2017, https://www.epilepsyresearch.org.uk/heat-as-a-seizure-trigger/, 1 page.
M. Shepherd, "Heat, Humidity, And Heart Disease Could Be A Deadly Mix", Dec. 18, 2017, https://www.forbes.com/sites/marshallshepherd/2017/12/18/heat-humidity-and-heart-disease-could-be-a-deadly-mix/#12c8d2711f72.

* cited by examiner

MANAGING HEALTH CONDITIONS USING PREVENTIVES BASED ON ENVIRONMENTAL CONDITIONS

BACKGROUND

1. Technical Field

Present invention embodiments relate to management of health conditions, and more specifically, to managing health conditions of users using preventives that are based on environmental conditions.

2. Discussion of the Related Art

Some health conditions, such as epilepsy or poor circulation, can become life-threatening when a person having the health condition is subjected to particular environmental conditions. For example, an individual's existing cardiac health condition may be exacerbated when the individual is exposed to high temperatures, poor air quality, and the like. While individuals can anticipate some environmental conditions and plan accordingly, it may be difficult to continually evaluate environmental conditions of locations, especially when a person has never been to a location before.

SUMMARY

According to one embodiment of the present invention, a computer system manages a health condition based on conditions of an environment. Health information of a user is analyzed to determine a health condition affected by environmental conditions. One or more events for the user are obtained based on personal information. The environmental conditions for one or more event locations are determined. One or more items are indicated for the user to attend the one or more events in order for the health condition to tolerate the environmental conditions of the one or more event locations. Embodiments of the present invention further include a method and program product for managing a health condition based on conditions of an environment in substantially the same manner described above.

BRIEF DESCRIPTION OF THE DRAWINGS

Generally, like reference numerals in the various figures are utilized to designate like components.

DETAILED DESCRIPTION

Figure 1:
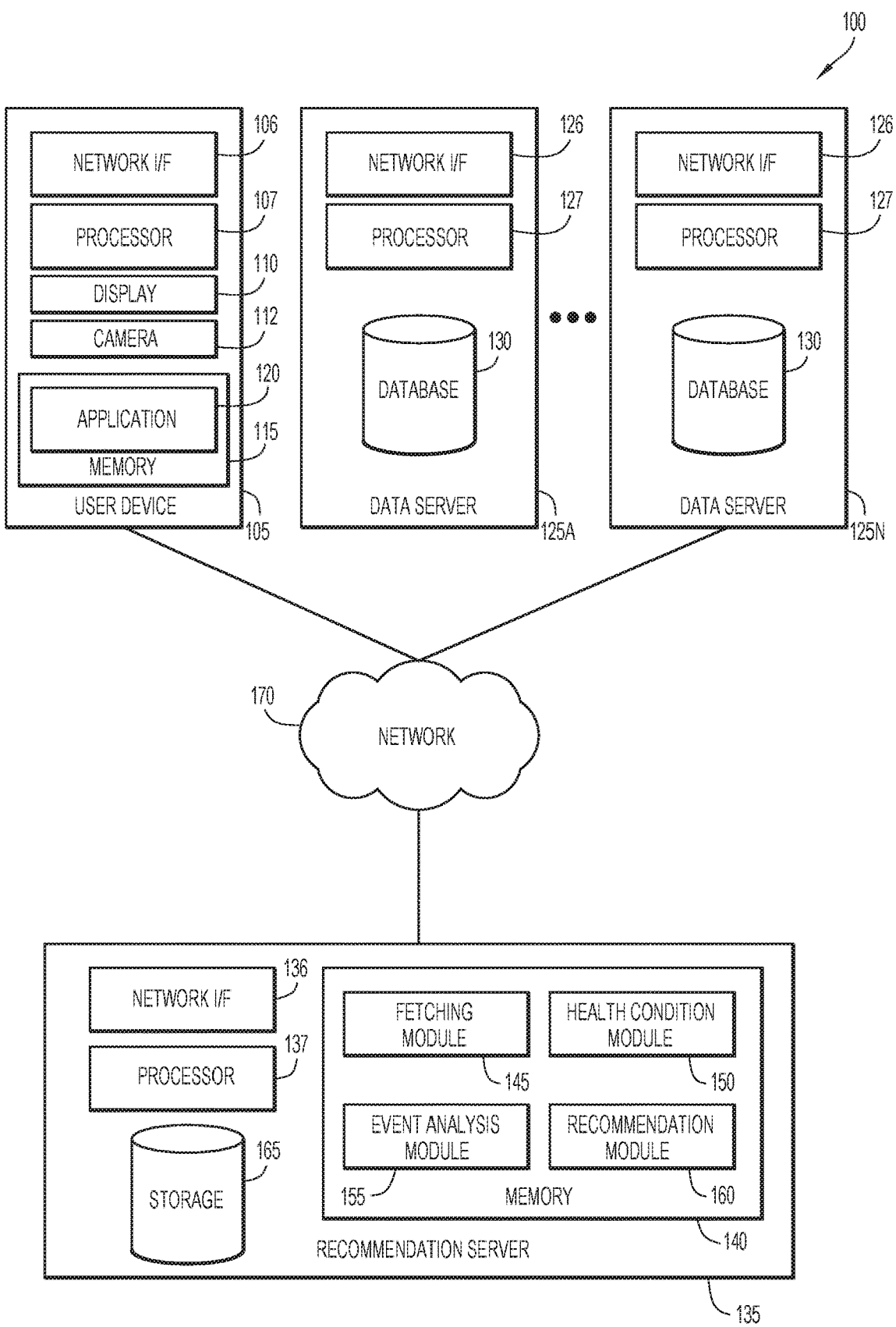
FIG. 1 is a block diagram depicting a computing environment for health condition management based on environmental conditions in accordance with an embodiment of the present invention.

Present invention embodiments relate to management of health conditions, and more specifically, to managing health conditions of users based on environmental conditions encountered by the users. While environmental conditions such as temperature extremes can exacerbate health conditions, the effects of such environmental conditions can often be mitigated using items such as medications or particular choices of apparel. However, it may be difficult for an individual to determine or predict present or future environmental conditions, especially for previously-unvisited locations. For example, a person who is visiting a city for the first time might be caught off-guard by the unusually warm air temperature of the city's subway system, which could potentially trigger a dangerous health episode.

Present invention embodiments manage health conditions of users by recommending preventive items to users based on the environmental conditions that the users are likely to encounter. In particular, any health conditions of a user that could make the user susceptible to environmental conditions are identified, and the user's personal information is analyzed to identify locations of events that the user is scheduled to attend. Environmental conditions for the event locations are determined, and a recommendation model recommends particular preventive items to the user that may mitigate the user's health condition while the user is exposed to the environmental conditions of the event location. For example, the recommendation model may recommend for a user to attend an event with a medication that will aid the user in tolerating an environmental condition associated with the event, such as smog or pollen. Environmental conditions may be determined based on data gathered from one or more locations, such as crowdsourced data, thereby providing an accurate assessment of a particular location's current environmental conditions. Moreover, outcomes of recommendations can be analyzed to improve the recommendation model over time.

It should be noted that references throughout this specification to features, advantages, or similar language herein do not imply that all of the features and advantages that may be realized with the embodiments disclosed herein should be, or are in, any single embodiment of the invention. Rather, language referring to the features and advantages is understood to mean that a specific feature, advantage, or characteristic described in connection with an embodiment is included in at least one embodiment of the present invention. Thus, discussion of the features, advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages will become more fully apparent from the following drawings, description and appended claims, or may be learned by the practice of embodiments of the invention as set forth hereinafter.

Present invention embodiments will now be described in detail with reference to the Figures. FIG. 1 is a block diagram depicting a computing environment 100 for health condition management based on environmental conditions in accordance with an embodiment of the present invention. As depicted, computing environment 100 includes a user device 105, one or more data servers 125A-125N, a recommendation server 135, and a network 170. It is to be understood that the functional division among components of computing environment 100 have been chosen for purposes of explaining present invention embodiments and is not to be construed as a limiting example.

User device 105 includes a network interface (I/F) 106, at least one processor 107, a display 110, a camera 112, and memory 115. Memory 115 may include application 120. User device 105 may include a laptop computer, a tablet computer, a netbook computer, a personal computer (PC), a desktop computer, a personal digital assistant (PDA), a smart phone, a thin client, or any programmable electronic device capable of executing computer readable program instructions. Network interface 106 enables components of user device 105 to send and receive data over a network, such as network 170. Users of user device 105 may include patients and/or health care professionals. In general, user device 105 may collect personal information about a user, such the user's schedule information, and may provide recommendations to a user to manage health conditions. Additionally or alternatively, user device 105 may collect health information of a user. User device 105 may include internal and external hardware components, as depicted and described in further detail with respect to FIG. 4.

Display 110 may include any electronic device capable of presenting information in a visual form. For example, display 110 may be a liquid crystal display (LCD), a cathode ray tube (CRT) display, a light-emitting diode (LED) display, an electronic ink display, and the like. Information relating to management of health conditions may be displayed to a user of user device 105 via display 110, including information such as health condition information, environmental condition information, personal information of a user, recommendations, and the like.

Camera 112 may include any image sensor capable of capturing image data, including still photographs and/or videos. A user of user device 105 may capture image data of event locations via camera 112. Captured image data may be shared with recommendation server 135 in order to evaluate actual environmental conditions against predicted environmental conditions.

Application 120 may include one or more modules or units to perform various functions of present invention embodiments described below. Application 120 may be implemented by any combination of any quantity of software and/or hardware modules or units, and may reside within memory 115 of user device 105 for execution by a processor, such as processor 107.

Application 120 may enable a user of user device 105 to input and receive data related to the management of health conditions. Application 120 may collect, or may otherwise be provided with, a user's personal information, including any information from calendars, schedules, email accounts, instant messaging accounts, Short Message Service (SMS) clients, social networking accounts, and the like, in order to collect personal information of a user. In some embodiments, a user of user device 105 may input data relating to a patient's health, such as any health-related conditions, feelings, sensations, etc. that are observed by the user.

Application 120 may receive recommendations from recommendation server 135 of one or more items that can mitigate a user's health condition when visiting an event location. Application 120 may present the one or more recommended items to a user via display 110 of user device 105. In some embodiments, a user may provide feedback via application 120 regarding the outcome of the user upon following a recommendation. For example, a user may indicate whether a recommended item was successful or unsuccessful in mitigating a health condition of the user. In some embodiments, a user may provide feedback that includes free-form text.

Data servers 125A-125N each include a network interface 126, at least one processor 127, and at least one database 130. In various embodiments of the present invention, data servers 125A-125N may each include a laptop computer, a tablet computer, a netbook computer, a personal computer (PC), a desktop computer, a personal digital assistant (PDA), a smart phone, or any programmable electronic device capable of executing computer readable program instructions. Network interface 126 enables components of each data server 125A-125N to send and receive data over a network, such as network 170. In an embodiment, one or more servers of data servers 125A-125N store data relating to electronic health records of patients. Additionally or alternatively, one or more servers of data servers 125A-125N store data relating to environmental conditions of one or more event locations, including temperature information, humidity information, population density or occupancy information, and/or air circulation information, including information relating to the heating, ventilation, and air conditioning (HVAC) equipment employed at event locations. Data servers 125A-125N may be servers that are associated with websites, such as social media websites, and/or applications, such as social media applications. Data servers 125A-125N may store data that can be accessed using conventional or other crowdsourcing techniques.

Database 130 may include any non-volatile storage media known in the art. For example, database 130 can be implemented with a tape library, optical library, one or more independent hard disk drives, or multiple hard disk drives in a redundant array of independent disks (RAID). Similarly, data on database 130 may conform to any suitable storage architecture known in the art, such as a file, a relational database, an object-oriented database, and/or one or more tables. In various embodiments, database 130 may store data relating to electronic health records of patients, environmental conditions of locations, social media data, and the like.

Recommendation server 135 includes a network interface 136, at least one processor 137, memory 140, and storage 165. Memory 140 includes a fetching module 145, a health condition module 150, an event analysis module 155, and a recommendation module 160. In various embodiments of the present invention, recommendation server 135 may include a laptop computer, a tablet computer, a netbook computer, a personal computer (PC), a desktop computer, a personal digital assistant (PDA), a smart phone, or any programmable electronic device capable of executing computer readable program instructions. Network interface 136 enables components of recommendation server 135 to send and receive data over a network, such as network 170. In general, recommendation server 135 and its modules may analyze a user's health information to identify health conditions, determine environmental conditions for event locations that the user may visit, and recommend items to enable a user to tolerate the environmental conditions of event locations. Recommendation server 135 may include internal and external hardware components, as depicted and described in further detail with respect to FIG. 4.

Fetching module 145, health condition module 150, event analysis module 155, and recommendation module 160 may include one or more modules or units to perform various functions of present invention embodiments described below. Fetching module 145, health condition module 150, event analysis module 155, and recommendation module 160 may be implemented by any combination of any quantity of software and/or hardware modules or units, and may reside within memory 140 of recommendation server 135 for execution by a processor, such as processor 137.

Fetching module 145 may obtain data from one or more sources, including data related to health conditions of users and data relating to environmental conditions of event locations. Fetching module 145 may access a server of data servers 125A-125N in order to obtain health information relating to a user, such as electronic health care records for the user. Additionally or alternatively, fetching module 145 may receive health information for a user from user device 105. In some embodiments, fetching module 145 receives an indication from user device 105 of a location (e.g., a particular server of data servers 125A-125N) where a user's electronic health records may be stored.

Fetching module 145 may perform conventional or other operations, such as web crawling or indexing, to obtain information relating to event locations from one or more sources, such as data servers 125A-125N. In some embodiments, fetching module 145 obtains information including, but not limited to, an event's time and date, duration, and location, event attendance information, and other event location information, including an age of a building in which an event is located, HVAC system information of an event location, dress code or other apparel recommendations/ requirements for an event location, and local regulations for an event location (e.g., building regulations of a municipality). Fetching module 145 may obtain information that describes environmental conditions of an event location by crowdsourcing the information from one or more social media websites, blogs, and the like. For example, fetching module 145 may identify any posts on a social media website that reference a particular auditorium in order to obtain data that can be used to determine the temperature conditions within the auditorium. Fetching module 145 may directly retrieve environmental condition information for an event location if possible; for example, a location may publish temperature and humidity information. In some embodiments, fetching module 145 utilizes an application programming interface (API) to access a computing system associated with an event location in order to retrieve environmental condition information.

Health condition module 150 may analyze a user's electronic health records to identify any health conditions of the user that may be affected by environmental conditions. Health record information of a user may be retrieved by fetching module 145. In some embodiments, health condition module 150 may analyze structured and/or unstructured health records of a patient to identify any terms, medical codes, or other identifiers that are associated with any health condition, including physical and mental conditions, that are affected by environmental conditions. Health conditions may include, but are not limited to, high blood pressure, epilepsy, brain issues, spine issues, lung issues, chronic fatigue syndrome, migraines, multiple sclerosis, autoimmune conditions, skin conditions, and the like.

Event analysis module 155 may analyze personal information of a user (e.g., information obtained from application 120) to identify any events that the user may be attending. Additionally, event analysis module 155 may analyze personal information and/or the data obtained by fetching module 145 to determine locations of the events and environmental conditions of event locations. Event analysis module 155 may identify events by analyzing a user's calendar or scheduler, social media website activity, instant messaging application activity, email data, and the like. Event analysis module 155 may utilize conventional or other natural language processing techniques to identify events that a user may attend, including the event's time, duration, and location.

When an event is identified, event analysis module 155 may determine, based on the location of the event, environmental conditions that can be expected at the time of the event. Environmental conditions may include temperature, humidity, population density, and air circulation. Event analysis module 155 may estimate one or more environmental conditions (e.g., temperature, humidity, etc.) based on the local season (e.g., time of year), and other factors, such as whether an event is indoors or outdoors, weather forecasts for the location of event, and the like. In some embodiments, event analysis module 155 determines population density or attendance at an event based on a headcount or similar listing or enumeration of attendees. Event analysis module 155 may determine an estimated attendance based on a number of users who have provided an indication of interest for an event on a social media website. In some embodiments, event analysis module 155 determines a population density for an event by dividing the number of attendees by the square footage of the event location, which can be obtained by accessing public records, construction plans, tax records or appraisal information, or other similar information associated with the event location.

In some embodiments, event analysis module 155 applies conventional or other natural language processing techniques to process data gathered by fetching module 145 in order to determine the environmental conditions of an event location. Event analysis module 155 may analyze crowdsourced data by performing natural language processing to determine whether certain areas are hot, humid, cold, and the like. In particular, event analysis module 155 may perform sentiment analysis and/or topic modeling to identify, within crowdsourced data, indications of environmental conditions of event locations.

Event analysis module 155 may identify the age of structures to determine whether a particular event location is likely to have good or poor air circulation. For example, an older subway station may have poorer air circulation than a newer subway station. Event analysis module 155 may similarly take into account building codes and regulations in determining the air circulation. For example, an event may be located in a municipality that has lenient air quality regulations, which may indicate poor air quality at the event location. Event analysis module 155 may determine air quality based on a current or historical air quality index for a location, or a current or historical pollen count for a location. In some embodiments, event analysis module 155 identifies other relevant information regarding an event location, such as an enforced or suggested dress code for an event location.

Recommendation module 160 may generate recommendations of one or more preventive items that may assist a user in tolerating the environmental conditions of an event location. Recommendation module 160 may include a recommendation model that maps health conditions and/or environmental conditions to preventive items that can be recommended to a user. In some embodiments, the recommendation model is a classification model.

Recommendation module 160 may process health condition information and environmental condition information to recommend an item to a user. Recommended preventive items may include medications, clothing, and any other items that may serve as a preventive against an environmental conditions. For example, a preventive item may include an over-the-counter or prescription medication, a particular outfit or clothing material to wear, or other items, such as a handheld fan, a mask, sunscreen, insect repellant, a portable oxygen concentrator, a cane, a wheelchair, and the like. For example, in response to event analysis module 155 determining that a user will be visiting an event location where the temperature is high, recommendation module 160 may recommend for the user to administer a particular dosage of a medication that treats aspects of the user's health condition, and may also recommend for the user to wear clothing made of a light and breathable fabric, such as a cotton t-shirt.

Recommendation module 160 may take into account any mandatory or suggested dress codes of an event location when making a recommendations. For example, recommendation module 160 may recommend that a user wear trousers instead of shorts, despite shorts being more favorable for a particular environmental condition, when the user is visiting an event location that does not allow visitors to wear shorts. Recommendation module 160 may also identify situations in which a user may be exposed to differences between indoor and outdoor environmental conditions, such as an event location that has both indoor and outdoor areas, or an indoor event that a user will attend before or after attending an outdoor event. For such differences in environmental conditions, recommendation module 160 may recommend that a user bring medications to act as preventives against health conditions exacerbated by the anticipated variety of environmental conditions, may recommend that a user bring layers of clothing that can be worn or removed according to a current event location's environmental conditions, etc.

Recommendation module 160 may receive feedback from a user that indicates an outcome for the user's health condition based on one or more items recommended to the user. A user may provide feedback, via application 120 of user device 105, to indicate whether a recommendation was successful or unsuccessful in mitigating the effects of environmental conditions on the user's health conditions. Recommendation module 160 may monitor user feedback to determine positive or negative outcomes of recommendations, and may adjust the recommendation model to recommend items that are associated with positive outcomes. Additionally or alternatively, recommendation module 160 may utilize conventional or other machine learning techniques, such as convolutional neural network (CNN) approaches and/or recurrent neural network (RNN) approaches, to learn items to indicate for health conditions. In some embodiments, one or more CNN models are used to recognize and classify features in images; a multi-layer neural network may analyze visual inputs for image classification, segmentation, and object detection. Visual input may include photos depicting users wearing various apparel items in indoor and/or outdoor environments. By analyzing whether a user appears to be pale, sweaty, or exhibiting facial expressions or other indicia of pain, a machine learning model can determine the accuracy of previous suggestions of recommendation module 160. In some embodiments, a RNN model can automatically provide captions or labels that describe contents of images. For example, images of users may be provided with labels that identify and describe important features in the images. Item recommendations can be learned based on user feedback and/or by using natural language processing to identify particular items that are associated with health conditions and/or environmental conditions.

Storage 165 may include any non-volatile storage media known in the art. For example, storage 165 can be implemented with a tape library, optical library, one or more independent hard disk drives, or multiple hard disk drives in a redundant array of independent disks (RAID). Similarly, data in storage 165 may conform to any suitable storage architecture known in the art, such as a file, a relational database, an object-oriented database, and/or one or more tables. Storage 165 may store data relating to managing health conditions based on environmental conditions, including health and personal information of users, event location information, environmental conditions of events, mappings of health conditions and environmental conditions to item recommendations, and the like.

Network 170 may include a local area network (LAN), a wide area network (WAN) such as the Internet, or a combination of the two, and includes wired, wireless, or fiber optic connections. In general, network 170 can be any combination of connections and protocols known in the art that will support communications between user device 105, data servers 125A-125N, and/or recommendation server 135 via their respective network interfaces in accordance with embodiments of the present invention.

Figure 2:
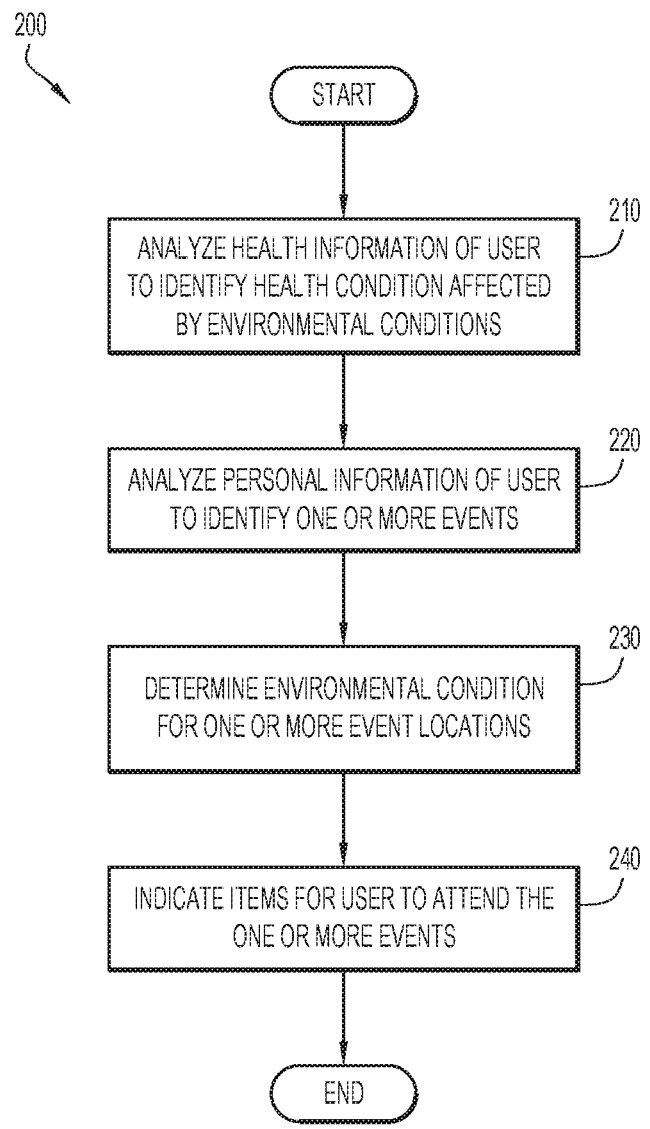
FIG. 2 is a flow chart depicting a method of managing health conditions based on environmental conditions in accordance with an embodiment of the present invention.

FIG. 2 is a flow chart depicting a method 200 of managing health conditions based on environmental conditions in accordance with an embodiment of the present invention.

Health information of a user is analyzed to identify health conditions affected by environmental conditions at operation 210. Fetching module 145 of recommendation server 135 may acquire health information from a user, such as a user's electronic health records, from one or more locations, such as a database 130 of any of data servers 125A-125N. Health condition module 150 may then analyze a user's health information to identify one or more health conditions of a user that may be affected by environmental conditions, such as high blood pressure, epilepsy, brain issues, spine issues, and the like.

Personal information of a user is analyzed to identify one or more events at operation 220. Fetching module 145 may obtain personal information of a user, including information obtained from a user's calendar, social media website activity of a user, instant messaging application activity of a user, emails of a user, and the like. Fetching module 145 may obtain personal information from user device 105 and/or from one or more of data servers 125A-125N. Event analysis module 155 may analyze the personal information of a user to identify any events that the user may be attending. In some embodiments, event analysis module 155 applies conventional or other natural language processing techniques, including topic modeling, to identify events that a user may attend.

Environmental conditions for one or more event locations are determined at operation 230. Fetching module 145 may obtain information about an event location by accessing one or more sources, such as data servers 125A-125N. For example, fetching module 145 may obtain information that includes an age of a structure where an event is located, discussions related to an event location on social media or blog postings, and the like. In some embodiments, fetching module 145 may directly access a computing device associated with an event location to receive data relating to the environmental conditions of the location. Fetched data may be analyzed with event analysis module 155 to determine the environmental conditions of an event location, such as the temperature, humidity, population density, and air circulation. Event analysis module 155 may apply conventional or other natural language processing to identify environmental conditions of an event.

One or more preventive items are indicated for a user to attend the one or more events in order for the user's health condition to tolerate the environmental conditions of the one or more event locations at operation 240. Recommendation module 160 may indicate items to a user based on the environmental conditions of an event location and/or the user's identified health conditions. Recommendation module 160 may employ a recommendation model that maps health conditions and/or environmental conditions to items that can be recommended to a user. Recommendations can include medications, clothing items, and other preventives, such as a particular amount of a medication to administer, a certain item of clothing (or quality of an item) to wear, a medical device, and the like. Recommendation module 160 may issue recommendations that account for a user visiting multiple event locations in succession; for example, recommendation module 160 may suggest for a user to bring layers of clothing to accommodate a user in a warm, indoors location and a cold, outdoors location. In some embodiments, a user's health conditions can indicate the user's tolerance for heat and cold, and recommendation module 160 may recommend items accordingly.

Figure 3:
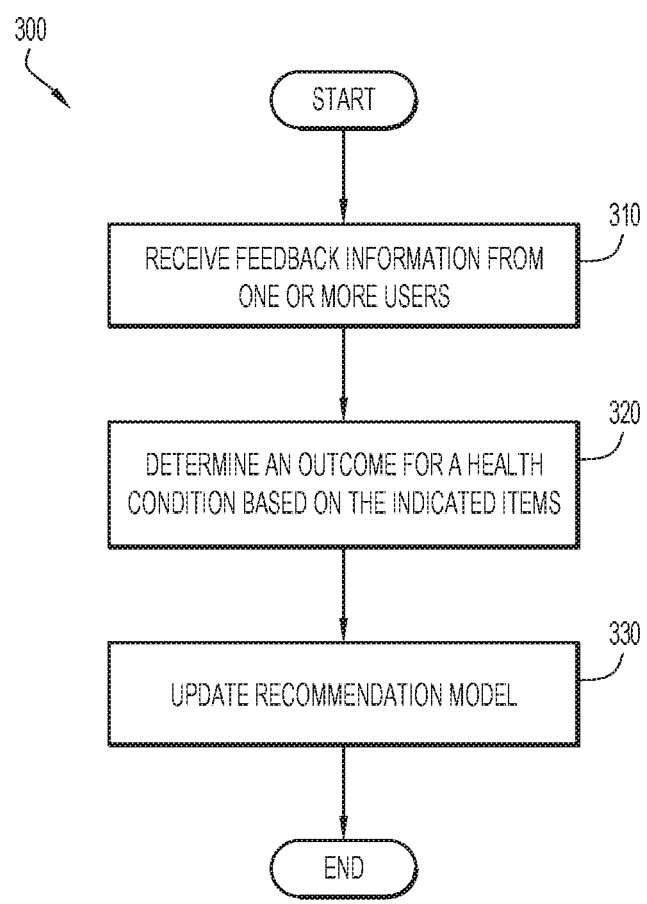
FIG. 3 is a flow chart depicting a method of updating a recommendation model in accordance with an embodiment of the present invention.

FIG. 3 is a flow chart depicting a method of updating a recommendation model in accordance with an embodiment of the present invention.

Feedback information from one or more users is received at operation 310. A user may provide, via application 120 of user device 105, feedback information that indicates the user's experience with regard to items recommended by recommendation module 160. In particular, a user may indicate whether a recommended item was successful or unsuccessful in mitigating the effects of environmental conditions on the user's health.

An outcome for a health condition is determined based on the indicated items at operation 320. Recommendation module 160 may monitor feedback from one or more users to determine outcomes of health conditions. In particular, recommendation module 160 may employ natural language processing techniques, such as sentiment analysis, to identify positive and negative outcomes based on the indicated items.

The recommendation model is updated at operation 330. Recommendation module 160 may update its recommendation model in view of positive and negative outcomes. In particular, recommended items that are associated with positive outcomes may be recommended with greater frequency, and items that are associated with negative outcomes may be recommended less. Additionally or alternatively, recommendation module 160 may employ machine learning techniques to learn items to recommend for health conditions of different users in order to optimize particular outcomes.

Figure 4:
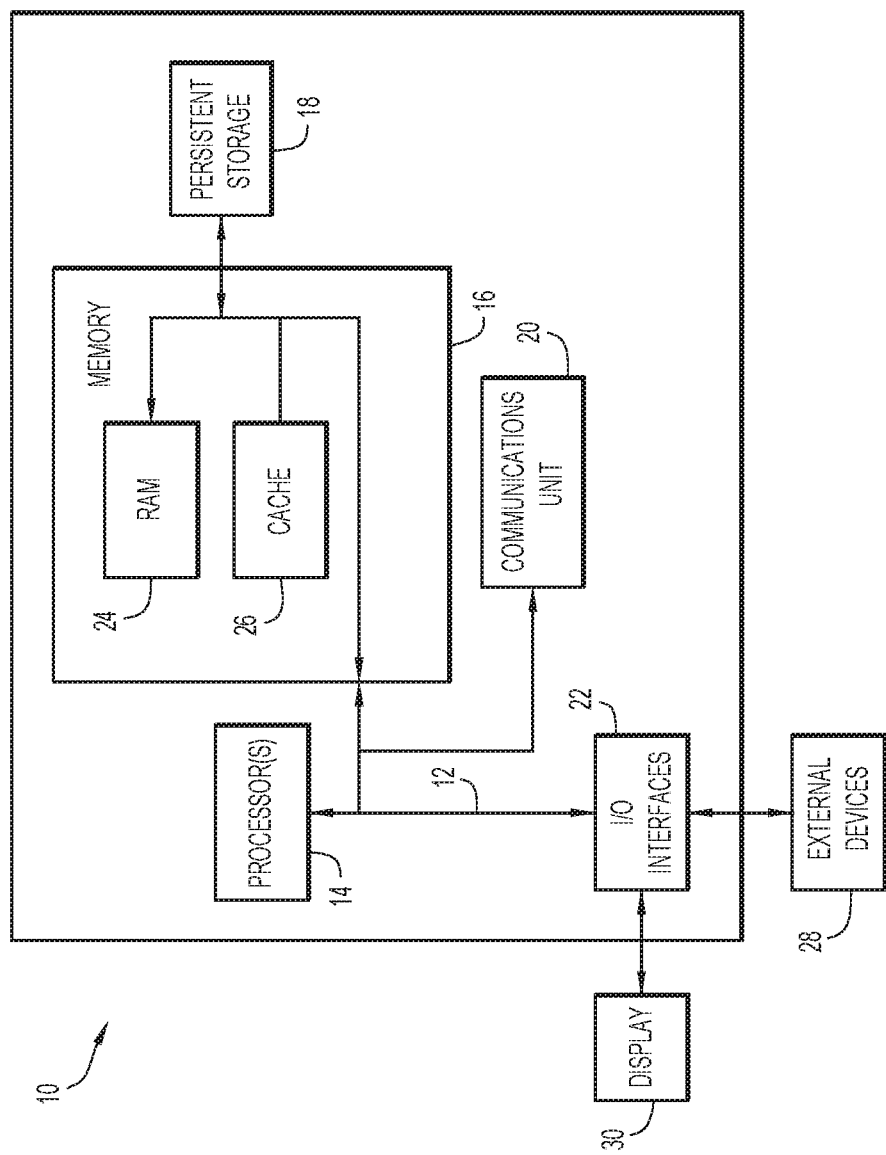
FIG. 4 is a block diagram depicting a computing device in accordance with an embodiment of the present invention.

FIG. 4 is a block diagram depicting components of a computer 10 suitable for executing the methods disclosed herein. Computer 10 may implement user devices 105, data server 125, and/or recommendation server 135 in accordance with embodiments of the present invention. It should be appreciated that FIG. 4 provides only an illustration of one embodiment and does not imply any limitations with regard to the environments in which different embodiments may be implemented. Many modifications to the depicted environment may be made.

As depicted, the computer 10 includes communications fabric 12, which provides communications between computer processor(s) 14, memory 16, persistent storage 18, communications unit 20, and input/output (I/O) interface(s) 22. Communications fabric 12 can be implemented with any architecture designed for passing data and/or control information between processors (such as microprocessors, communications and network processors, etc.), system memory, peripheral devices, and any other hardware components within a system. For example, communications fabric 12 can be implemented with one or more buses.

Memory 16 and persistent storage 18 are computer readable storage media. In the depicted embodiment, memory 16 includes random access memory (RAM) 24 and cache memory 26. In general, memory 16 can include any suitable volatile or non-volatile computer readable storage media.

One or more programs may be stored in persistent storage 18 for execution by one or more of the respective computer processors 14 via one or more memories of memory 16. The persistent storage 18 may be a magnetic hard disk drive, a solid state hard drive, a semiconductor storage device, read-only memory (ROM), erasable programmable read-only memory (EPROM), flash memory, or any other computer readable storage media that is capable of storing program instructions or digital information.

The media used by persistent storage 18 may also be removable. For example, a removable hard drive may be used for persistent storage 18. Other examples include optical and magnetic disks, thumb drives, and smart cards that are inserted into a drive for transfer onto another computer readable storage medium that is also part of persistent storage 18.

Communications unit 20, in these examples, provides for communications with other data processing systems or devices. In these examples, communications unit 20 includes one or more network interface cards. Communications unit 20 may provide communications through the use of either or both physical and wireless communications links.

I/O interface(s) 22 allows for input and output of data with other devices that may be connected to computer 10. For example, I/O interface 22 may provide a connection to external devices 28 such as a keyboard, keypad, a touch screen, and/or some other suitable input device. External devices 28 can also include portable computer readable storage media such as, for example, thumb drives, portable optical or magnetic disks, and memory cards.

Software and data used to practice embodiments of the present invention can be stored on such portable computer readable storage media and can be loaded onto persistent storage 18 via I/O interface(s) 22. I/O interface(s) 22 may also connect to a display 30. Display 30 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Data relating to management of health conditions based on environmental conditions (e.g., personal information of users, health information of users, event information, event location information, environmental information, recommendation information, crowdsourced information, feedback information, etc.) may be stored within any conventional or other data structures (e.g., files, arrays, lists, stacks, queues, records, etc.) and may be stored in any desired storage unit (e.g., database, data or other repositories, queue, etc.). The data transmitted between user device 105, data servers 125A-125N, and/or recommendation server 135 may include any desired format and arrangement, and may include any quantity of any types of fields of any size to store the data. The definition and data model for any datasets may indicate the overall structure in any desired fashion (e.g., computer-related languages, graphical representation, listing, etc.).

Data relating to management of health conditions based on environmental conditions (e.g., personal information of users, health information of users, event information, event location information, environmental information, recommendation information, crowdsourced information, feedback information, etc.) may include any information provided to, or generated by, user device 105, data servers 125A-125N, and/or recommendation server 135. Data relating to management of health conditions based on environmental conditions may include any desired format and arrangement, and may include any quantity of any types of fields of any size to store any desired data. The data relating to management of health conditions based on environmental conditions may include any data collected about entities by any collection mechanism, any combination of collected information, and any information derived from analyzing collected information.

The present invention embodiments may employ any number of any type of user interface (e.g., Graphical User Interface (GUI), command-line, prompt, etc.) for obtaining or providing information (e.g., data relating to management of health conditions based on environmental conditions), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

It will be appreciated that the embodiments described above and illustrated in the drawings represent only a few of the many ways of managing health conditions using preventives based on environmental conditions.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, application 120, fetching module 145, health condition module 150, event analysis module 155, recommendation module 160, etc.). These systems may include any types of monitors and input devices (e.g., keyboard, mouse, voice recognition, etc.) to enter and/or view information.

It is to be understood that the software (e.g., browser software, communications software, server software, application 120, fetching module 145, health condition module 150, event analysis module 155, recommendation module 160, etc.) of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments (e.g., browser software, communications software, server software, application 120, fetching module 145, health condition module 150, event analysis module 155, recommendation module 160, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., data relating to management of health conditions based on environmental conditions). The database system may be implemented by any number of any conventional or other databases, data stores or storage structures (e.g., files, databases, data structures, data or other repositories, etc.) to store information (e.g., data relating to management of health conditions based on environmental conditions). The database system may be included within or coupled to the server and/or client systems. The database systems and/or storage structures may be remote from or local to the computer or other processing systems, and may store any desired data (e.g., data relating to management of health conditions based on environmental conditions).

The present invention embodiments may employ any number of any type of user interface (e.g., Graphical User Interface (GUI), command-line, prompt, etc.) for obtaining or providing information (e.g., data relating to management of health conditions based on environmental conditions), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for any number of applications in the relevant fields, including, but not limited to, managing health conditions of users by recommending items that mitigate the effects of environmental conditions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for managing a health condition based on conditions of an environment, the computer-implemented method comprising:
    analyzing, via a processor, health information of a user to determine a health condition affected by environmental conditions;
    obtaining, via the processor, one or more events for the user based on personal information;
    determining, via the processor, the environmental conditions at one or more event locations for the one or more events, wherein the environmental conditions include population density based on an attendance level for the one or more events, and air circulation quality; and
    recommending, via the processor and using a machine learning model, one or more preventive items for the user to attend the one or more events in order for the health condition to tolerate the environmental conditions of the one or more event locations;
    analyzing, via a processor, user feedback to determine an experience of the user with regard to the one or more recommended preventive items,
    wherein the machine learning model learns associations between the one or more preventive items, the health condition of the user and the environmental conditions by:
        recognizing and classifying features in images of users to identify particular preventive items; and
        identifying particular preventive items by performing natural language processing of user feedback, and updating based on positive or negative outcomes to the user based on previous recommendations.

2. The computer-implemented method of claim 1, wherein the health condition includes one or more from a group of high blood pressure, epilepsy, brain issues, and spine issues.

3. The computer-implemented method of claim 1, wherein the environmental conditions of the one or more event locations further include one or more from a group of temperature, and humidity.

4. The computer-implemented method of claim 1, wherein the one or more events include a plurality of events that occur at different locations, and the environmental conditions include difference in temperatures encountered when traveling between the different locations.

5. The computer-implemented method of claim 1, wherein the one or more preventive items include one or more from a group of clothes and medication.

6. The computer-implemented method of claim 1, further comprising: learning, via the processor, the one or more preventive items to indicate for health conditions of different users to optimize for positive outcomes.

7. A computer system for managing a health condition based on conditions of an environment, the computer system comprising:
    one or more computer processors;
    one or more computer readable storage media;
    program instructions stored on the one or more computer readable storage media for execution by at least one of the one or more computer processors, the program instructions comprising instructions to:
        analyze health information of a user to determine a health condition affected by environmental conditions;
    obtain one or more events for the user based on personal information;
    determine the environmental conditions at one or more event locations for the one or more events, wherein the environmental conditions include population density based on an attendance level for the one or more events, and air circulation quality; and
    recommend, using a machine learning model, one or more preventive items for the user to attend the one or more events in order for the health condition to tolerate the environmental conditions of the one or more event locations analyze user feedback to determine the an experience of the user with regard to the one or more recommended preventive items, wherein the machine learning model learns associations between the one or more preventive items, the health condition of the user and the environmental conditions by:
  recognizing and classifying features in images of users to identify particular preventive items; and
  identifying particular preventive items by performing natural language processing of user feedback, and updating based on positive or negative outcomes to the user based on previous recommendations.

8. The computer system of claim 7, wherein the health condition includes one or more from a group of high blood pressure, epilepsy, brain issues, and spine issues.

9. The computer system of claim 7, wherein the environmental conditions of the one or more event locations further include one or more from a group of temperature, and humidity.

10. The computer system of claim 7, wherein the one or more events include a plurality of events that occur at different locations, and the environmental conditions include difference in temperatures encountered when traveling between the different locations.

11. The computer system of claim 7, wherein the one or more preventive items include one or more from a group of clothes and medication.

12. The computer system of claim 7, wherein the program instructions further comprise instructions to: learn the one or more preventive items to indicate for health conditions of different users to optimize for positive outcomes.

13. A computer program product for managing a health condition based on conditions of an environment, the computer program product comprising one or more computer readable storage media collectively having program instructions embodied therewith, the program instructions executable by a computer to cause the computer to:
  analyze health information of a user to determine a health condition affected by environmental conditions;
  obtain one or more events for the user based on personal information;
  determine the environmental conditions at one or more event locations for the one or more events, wherein the environmental conditions include population density based on an attendance level for the one or more events, and air circulation quality; and
  recommend, using a machine learning model, one or more preventive items for the user to attend the one or more events in order for the health condition to tolerate the environmental conditions of the one or more event locations
  analyze user feedback to determine an experience of the user with regard to the one or more recommended preventive items,
  wherein the machine learning model learns associations between the one or more preventive items, the health condition of the user and the environmental conditions by:
    recognizing and classifying features in images of users to identify particular preventive items; and
    identifying particular preventive items by performing natural language processing of user feedback, and updating based on positive or negative outcomes to the user based on previous recommendations.

14. The computer program product of claim 13, wherein the health condition includes one or more from a group of high blood pressure, epilepsy, brain issues, and spine issues.

15. The computer program product of claim 13, wherein the environmental conditions of the one or more event locations further include one or more from a group of temperature, and humidity.

16. The computer program product of claim 13, wherein the one or more events include a plurality of events that occur at different locations, and the environmental conditions include difference in temperatures encountered when traveling between the different locations.

17. The computer program product of claim 13, wherein the one or more preventive items include one or more from a group of clothes and medication.

* * * * *